(12) United States Patent
Noh et al.

(10) Patent No.: US 10,993,904 B2
(45) Date of Patent: May 4, 2021

(54) TRANSPLANTATION IMPLANT FOR PROMOTING HAIR GROWTH

(71) Applicants: INSCOBEE INC., Seoul (KR); Seung-Kwon Noh, Seoul (KR)

(72) Inventors: Seung-Kwon Noh, Seoul (KR); Jung-Soo Park, Seoul (KR); In-Soo You, Seoul (KR)

(73) Assignee: Inscobee Inc., Seoul (KR)

( * ) Notice: Subject to any disclaimer, the term of this patent is extended or adjusted under 35 U.S.C. 154(b) by 11 days.

(21) Appl. No.: 15/852,841

(22) Filed: Dec. 22, 2017

(65) Prior Publication Data

US 2018/0177716 A1    Jun. 28, 2018

(30) Foreign Application Priority Data

Dec. 23, 2016  (KR) .................. 10-2016-0178521
Aug. 22, 2017  (KR) .................. 10-2017-0106012

(51) Int. Cl.
*A61K 8/98*      (2006.01)
*A61Q 7/00*      (2006.01)
*A61P 17/14*     (2006.01)

(52) U.S. Cl.
CPC .............. *A61K 8/982* (2013.01); *A61P 17/14* (2018.01); *A61Q 7/00* (2013.01)

(58) Field of Classification Search
CPC ............ A61K 8/982; A61P 17/14; A61Q 7/00
USPC ....................................................... 424/93.7
See application file for complete search history.

(56) References Cited

U.S. PATENT DOCUMENTS

| 2010/0034856 A1* | 2/2010 | Gho ................. A61K 8/985 424/401 |
| 2010/0129328 A1 | 5/2010 | Sing et al. |
| 2012/0245705 A1* | 9/2012 | Hasilo ............. A61M 39/0247 623/23.72 |
| 2016/0289641 A1 | 10/2016 | Sung |

FOREIGN PATENT DOCUMENTS

| JP | 2003081866 A | 3/2003 |
| JP | 2005528916 A | 9/2005 |
| JP | 2015157146 A | 9/2015 |
| KR | 20090040414 A | 4/2009 |
| KR | 20120089235 A | 8/2012 |
| KR | 20140125735 A | 10/2014 |
| KR | 10-1484033 B1 | 1/2015 |
| KR | 10-1498201 B1 | 2/2015 |
| WO | WO 2014/140913 * | 9/2014 |
| WO | 2016006788 A1 | 1/2016 |
| WO | 2016086020 A1 | 6/2016 |
| WO | 2016147005 A1 | 9/2016 |
| WO | 2016159721 A1 | 10/2016 |

OTHER PUBLICATIONS

Eslaminejad et al., Amniotic Fluid Stem Cells and Their Application in Cell-Based Tissue Regeneration, International Journal of Fertility and Sterility vol. 6, No. 3, Oct.-Dec. 2012, pp. 147-156.*
Pisciotta et al., Human Serum Promotes Osteogenic Differentiation of Human Dental Pulp Stem Cells In Vitro and In Vivo, PLOS One, vol. 7, Iss. 11, Nov. 2012, pp. 1-11.*
Luo et al., Potential Roles of Dental Pulp Stem Cells in Neural Regeneration and Repair, Stem Cells International, vol. 2018, Article ID 1731289, pp. 1-15.*
Park et al., Cytokine Secretion Profiling of Human Mesenchymal Stem Cells by Antibody Array, International Journal of Stem Cells, vol. 2, No. 1,(2009), p. 59-68.*
Hass et al., Different populations and sources of human mesenchymal stem cells (MSC): A comparison of adult and neonatal tissue-derived MSC, Cell Communication and Signaling, 9(12) (2011) p. 1-14.*
Japanese Office Action dated Aug. 17, 2018, issued in corresponding Japanese Patent Application No. 2017-246459, citing the above references.
Korean Office Action dated Oct. 22, 2018, issued in corresponding Korean Patent Application No. 10-2017-0106012, citing the above references.

* cited by examiner

*Primary Examiner* — Jennifer M. H. Tichy
(74) *Attorney, Agent, or Firm* — Servilla Whitney LLC

(57) ABSTRACT

The present disclosure relates to a transplantation implant that includes stem cells having an ability of secreting a cytokine that having a hair-growing function.

15 Claims, 17 Drawing Sheets

Attached cell culture

Cell culture in theracyte

TRANSPLANTATION IMPLANT FOR PROMOTING HAIR GROWTH

CROSS-REFERENCE TO RELATED APPLICATION

This application claims priority to and the benefit of Korean Patent Application No. 10-2016-0178521, filed on Dec. 23, 2016, and Korean Patent Application No. 10-2017-0106012, filed on Aug. 22, 2017, the present disclosures of which are incorporated herein by reference in its entirety.

BACKGROUND

1. Field of the Invention

The present disclosure relates to an implant for promoting hair growth.

2. Discussion of Related Art

Hair plays various roles such as protecting the head, affecting one's appearance, and maintaining the temperature of the head in the human body. Although hair is not a vital organ, hair is an important part of the body that is a barometer of health and affects one's appearance. Although hair loss has been recognized as a sign of aging, nowadays, it is being revealed that hair loss has various causes such as stress, westernized diet, nutritional imbalance, and changes in social activities as well as various genetic factors.

Hair grows from follicles having a structure in which skin is depressed due to continuous proliferation of keratinocytes at the base of the scalp. A hair growth cycle includes various phases. Hair grows and falls out repeatedly in accordance with the hair growth cycle that includes four phases: anagen (a growing phase) which is a phase that 90% of hair follicles undergo; catagen (a transitional phase) in which growth of hair stops and hair roots shrink; telogen (a resting phase) in which hair bulbs dry and become club hair; and exogen.

Causes of hair loss include genetic factors, stress, aging, and the like. A typical mechanism of hair loss is one in which a male hormone testosterone (T), is converted into dihydrotestosterone (DHT) due to $5\alpha$-reductase (RD), causing the shrinkage of hair follicles in scalp, and resulting in hair loss. DHT increases with age, and the increase in DHT causes a delay in protein synthesis. The delay in protein synthesis is considered to cause the proportion of follicles in the telogen phase to increase, and the increase accelerates hair loss. Also, stem cells that secrete keratin at the dermal papilla of hair follicles are destroyed with age, and the supply of stem cells decreases. In this way, hair loss is accelerated.

Hair growth has a cyclic pattern. That is, hair grows and falls out repeatedly throughout the hair growth cycle that includes four phases: anagen (the growing phase) which is a phase that 90% of hair follicles undergo; catagen (the transitional phase) in which the growth of hair stops and hair roots shrink; telogen (the resting phase) in which hair bulbs dry and become club hair; and exogen. In particular, during the catagen phase, many follicles undergo apoptosis and enter the telogen phase, reduing the size of the follicles.

Methods developed for alleviating and treating hair loss include a method of applying a substance (a synthetic substance, a natural product, a cell culture medium, an extract thereof, or the like) that promotes hair growth, a method of transplanting hair, a method of infusing one's own stem cells, or the like. For example, minoxidil lotion is widely used as treatment for hair loss; a composition for preventing hair loss or improving hair growth that includes a codium contractum extract as an active ingredient is disclosed in Korean Patent Registration No. 10-1498201; and a composition for preventing hair loss or promoting hair growth that includes an extract of shell Arachis hypogaea Linne is disclosed in Korean Patent Registration No. 10-1484033.

Nowadays, there is a growing interest in treatment using a stem cell culture medium. The growing interest is due to the fact that culture media using mesenchymal stem cells contain abundant growth factors that promote hair growth.

However, when hair roots disappear and follicles have to be newly formed, difficulties may arise from limited effectiveness, repeated application of a substance for promoting hair growth, or repeated infusion of one's own stem cells. Although continuous supply of growth factors related to hair growth is important to produce hair again, the method of infusing one's own stem cells or applying a substance for promoting hair growth is intermittently performed and thus has difficulty in continuously supplying the growth factors. Also, mesenchymal stem cells are difficult to continuously grow.

Thus, during research on a method of continuously supplying growth factors required for hair growth into a living body, the present inventors confirmed that long-term effectiveness of stem cells is possible by transplanting stem cells cultured under specific conditions into the living body using a transplantation implant in order to continuously supply stem cell growth promoting factors such a basic fibroblast growth factor (bFGF) into the living body and induce growth of stem cells in the dermal papilla of hair follicles, accomplishing the present disclosure.

SUMMARY OF THE INVENTION

An objective of the present disclosure is to provide a transplantation implant for promoting hair growth and/or alleviating and treating hair loss.

To achieve the above objective, the present disclosure provides a transplantation implant that includes stem cells having an ability to secrete cytokine having a hair-growing function.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
FIG. 1A illustrates a method of culturing reprogrammed amniotic fluid-derived mesenchymal stem cell with Nanog (AF-N) using an attached cell culture.
FIG. 1B illustrates a method of culturing reprogrammed amniotic fluid-derived mesenchymal stem cell with Nanog (AF-N) using a cell culture in TheraCyte™.
Figure 1:
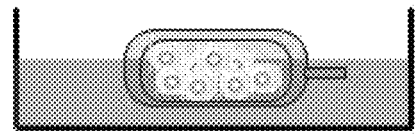

The present disclosure relates to a transplantation implant for transplanting into a living body that includes stem cells having an ability to secrete cytokine having a hair-growing function.

The present disclosure relates to a method of preparing a transplantation implant for alleviating hair loss that includes injecting stem cells having an ability to secrete cytokine having a hair-growing function into a transplantation implant.

The present disclosure relates to a method of preparing a transplantation implant for treating hair loss that includes injecting stem cells having an ability to secrete cytokine having a hair-growing function into a transplantation implant.

The present disclosure relates to a method of preparing a transplantation implant for promoting hair growth that includes injecting stem cells having an ability to secrete cytokine having a hair-growing function into a transplantation implant.

The present disclosure relates to a method of alleviating hair loss that includes transplanting an implant of the present disclosure in a living body.

The present disclosure relates to a method of treating hair loss that includes transplanting an implant of the present disclosure in a living body.

The present disclosure relates to a method of promoting hair growth that includes transplanting an implant of the present disclosure in a living body.

The present disclosure relates to a use of a transplantation implant that includes stem cells having an ability to secrete cytokine having a hair-growing function for treating hair loss, alleviating hair loss, or promoting hair growth.

Hereinafter, the present disclosure will be described in detail.

Stem Cells Having an Ability to Secrete Cytokine Having a Hair-Growing Function

Preferably, stem cells having an ability to secrete cytokine having a hair-growing function of the present disclosure are amniotic fluid-derived stem cells. This is because cells in an amniotic fluid secrete growth hormones. Preferably, the stem cells having an ability to secrete cytokine having a hair-growing function of the present disclosure are reprogrammed amniotic fluid stem cells. Also, preferably, the stem cells having an ability to secrete cytokine having a hair-growing function of the present disclosure are fetal-derived mesenchymal stem cells. More preferably, the stem cells having an ability to secrete cytokine having a hair-growing function of the present disclosure are fetal-derived reprogrammed mesenchymal stem cells.

The reprogrammed stem cells are formed using a known reprogramming method, and the method of forming the reprogrammed stem cells is not particularly limited. For example, the reprogrammed stem cells of the present disclosure may be formed by introducing a reprogramming factor into mesenchymal stem cells. The type of reprogramming factor is also not particularly limited, but using a proven W reprogramming factor is preferable in terms of safety and efficiency. For example, the reprogrammed stem cells of the present disclosure may be prepared using an Oct4 gene, a Klf gene, a Myc gene, a Sox gene, a Nanog gene, or the like as the reprogramming factor. Preferably, the reprogrammed stem cells of the present disclosure may be formed using the Nanog gene. The reprogrammed stem cells of the present disclosure promote characteristics such as a longer growth period, a higher number of divisions from growth, and increased secretion of growth factors in comparison to stem cells that are not reprogrammed.

The cytokine that having a hair-growing function refers to cytokine having effects of promoting hair growth, treating hair loss, suppressing hair loss, and alleviating hair loss. The cytokine may be selected from the group consisting of a basic fibroblast growth factor (bFGF), a platelet-derived growth factor (PDGF)-AA, an insulin-like growth factor (IGF), and Wnt7a.

Preferably, the stem cells are stem cells cultured under hypoxia. Here, the hypoxia refers to a condition in which oxygen concentration is lower than that at atmospheric pressure, preferably a condition in which an oxygen concentration is at 0.01% to 8%, more preferably a condition in which an oxygen concentration is at 0.05% to 5%, and still more preferably a condition in which an oxygen concentration is at 0.10% to 3%.

Here, the culture may be a culture in a transplantation implant or a culture in a general attached cell culture, and is preferably a culture in a general attached cell culture.

Transplantation Implant

The transplantation implant of the present disclosure is a thin-film polymer chamber prepared as a biocompatible membrane. The transplantation implant is a container for transplantation in a living body, that is, a bio-transplant container, has a space into which cells may be injected, and secretes substances formed by the stem cells, particularly, cytokines, to outside the implant via a thin film. Preferably, the implant has a neovascularization function that protects the implant from being rejected by a recipient of the stem cell transplantation and induces formation of capillary vessels close to membranes when the implant is transplanted in the hypodermis. Through the neovascularization function, the implant provides nutrition and blood to stem cells in the thin film. Preferably, the implant is prepared with a substance that is biocompatible, i.e., does not cause an immune reaction. The substance is a known substance such as polyurethane. Preferably, the implant has a porous surface in which a plurality of fine holes are formed. Here, the holes preferably have a size through which large substances such as cells are unable to pass but protein or nutrients are able to enter and exit. Therefore, because stem cells injected into the implant are unable to exit the implant via the holes, cancer caused by the stem cells is prevented while growth-promoting factors secreted by the stem cells are released into the blood such that a blood vessel is formed and oxygen and nutrients are supplied into the implant. In this way, a survival period of the stem cells significantly increases. The implant can be easily removed even if it has been a long time since transplantation. A commercially available product that satisfies the above conditions may be purchased and used as the implant, or the implant may be manufactured and used. For example, the implant is preferably TheraCyte™.

The transplantation implant of the present disclosure is for treating or alleviating hair loss. Also, the transplantation implant of the present disclosure is for promoting hair growth. Here, the transplantation implant of the present disclosure may be used for treating or alleviating hair loss due to aging. Also, the transplantation implant of the present disclosure may be used for promoting hair growth in the parents or people who suffer from hair loss due to aging.

The transplantation implant of the present disclosure may include $1.0 \times 10^3$ to $1.0 \times 10^{10}$ stem cells. Here, the cultured stem cells themselves are injected into the implant. However, the present disclosure relates to allowing the stem cells themselves to act in a living body for a long period of time and does not relate to the injection of culture media of stem cells into the implant. Because the stem cells of the present disclosure are transplanted in the implant by being injected into the implant having a permeable membrane, the stem cells can receive oxygen and nutrients required for survival from the blood of a recipient of the stem cell transplantation. Also, rather than injecting culture media in the implant, injecting more stem cells is considerably more effective in promoting hair growth and preventing/alleviating/treating hair loss.

Because the transplantation implant of the present disclosure is transplanted in a living body after the stem cells of the present disclosure are injected into the transplantation implant, hair growth can be promoted without immune rejection or a risk of forming cancer cells.

Preferably, the transplantation implant of the present disclosure is transplanted in a living body, preferably under the scalp (hypodermis). Here, a recipient of the transplantation implant of the present disclosure is a living organism including a human and is, particularly, a person who suffers from hair loss.

Injecting Stem Cells Having an Ability to Secrete Cytokine Having a Hair-Growing Function into the Transplantation Implant The present disclosure relates to a method of preparing a transplantation implant for promoting hair growth/treating hair loss/alleviating hair loss/suppressing hair loss that includes injecting stem cells having an ability to secrete cytokine having a hair-growing function into the transplantation implant. A conventional method of injecting cells into an implant may be used as the injection method itself, and the injection method is not particularly limited.

Advantages and features of the present disclosure and a method of achieving the same should become clear with reference to examples described in detail below. However, the present disclosure is not limited to examples disclosed below and is realized in various other forms. The present examples make the present disclosure complete and are provided to completely inform one of ordinary skill in the art to which the present disclosure pertains of the scope of the disclosure. The present disclosure is defined only by the scope of the claims.

Substances and Method

Experimental Animal 6-week-old C57BL6 mice were used as experimental animals. For an aged model test, 13-week-old or older C57BL/6 mice were used.

Reprogrammed Amniotic Fluid-Derived Mesenchymal Stem Cell with Nanog (AF-N)

Reprogrammed amniotic fluid-derived mesenchymal stem cell with nanog; (Hereinafter AF-N) was prepared by introducing a Nanog gene into amniotic fluid-derived fetal mesenchymal stem cells using a retrovirus vector and inducing overexpression of the Nanog gene. The above reprogrammed amniotic fluid-derived mesenchymal stem cell with nanog is referred as "AF-N".

Culturing Stem Cells

The amniotic fluid stem cells were cultured in a Dulbecco's Modified Eagle's medium (DMEM), a 10% fetal bovine serum (FBS) medium, 1% penicillin/streptomycin (P/S) medium, 1% L-glutamine medium, 4 ng/ml bFGF medium, 5 ng/ml selenium medium, and 50 ug/ml vitamin C medium.

Injection of Amniotic Fluid Stem Cells into TheraCyte™

Amniotic fluid stem cell groups were cultured in a 100 mm-cell culture dish until 70% to 80% of a surface of an attached culture container was covered, the number of cells was counted, $1.0 \times 10^7$ cells were suspended in 20 ul of low-glucose DMEM, and then a 22G needle was used to inject the cells into TheraCyte™. Then, an inlet was sealed with a high-strength adhesive.

TheraCyte™ Transplantation

After anesthetizing the mice, a hole of about 10 mm was formed in the right side of the back of the mice, and then TheraCyte™ was injected through the hole. Then, the wound was sutured by sewing up the wound with a suturing silk thread or using a wound clip.

Cell Counting Kit (CCK)

After sacrificing the mice of an experimental group and separating the transplanted TheraCyte™ from the mice, an outer portion of the TheraCyte™ was washed clean with phosphate-buffered saline (PBS). Then, an AF growth medium and 100 ul of the CCK were mixed, and the mixture was cultured for 30 minutes. After harvesting the cultured medium, an absorbance at a wavelength of 450 nm was measured.

EXAMPLE 1

Amniotic fluid stem cells were acquired by culturing amniotic fluid stem cells, in which a Nanog gene is not introduced, under normoxia.

EXAMPLE 2

Amniotic fluid stem cells were acquired by culturing AF-N under normoxia.

EXAMPLE 3

Amniotic fluid stem cells were acquired by culturing amniotic fluid stem cells, to which a Nanog gene is not introduced, under hypoxia (low oxygen) at an oxygen concentration of 1%.

EXAMPLE 4

Amniotic fluid stem cells were acquired by culturing AF-N under hypoxia (low oxygen) at an oxygen concentration of 1%.

EXPERIMENTAL EXAMPLE 1

Confirmation of Cytokine bFGF Secretion of AF-N Injected into TheraCyte™

Differences in concentrations of bFGF, a cytokine having a hair-growing function, were evaluated among the acquired conditioned media according to the methods of culturing AF-N. Specifically, the cell counts of AF-N stem cells were varied to be $1.0 \times 10^5$, $4 \times 10^5$, and $1.0 \times 10^6$, and the bFGF concentrations in the conditioned media were measured using an enzyme-linked immunosorbent assay (ELISA) method when AF-N was cultured using an attached cell culture, which is a general method for stem cell culturing (FIG. 1A), and when AF-N was cultured using a cell culture in TheraCyte™ (FIG. 1B).

Figure 2:
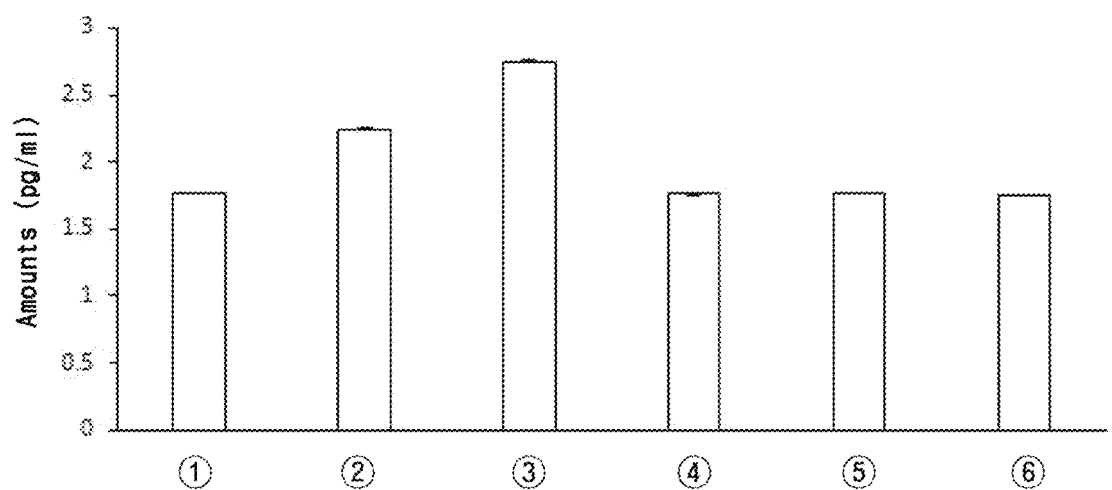
FIG. 2 shows concentrations of a basic fibroblast growth factor (bFGF) in conditioned media according to culturing methods (1: $1.0 \times 10^5$ AF-N cultured using an attached cell culture; 2: $4 \times 10^5$ AF-N cultured using an attached cell culture; 3: $1.0 \times 10^6$ AF-N cultured using an attached cell culture; 4: $1.0 \times 10^5$ AF-N cultured using a cell culture in TheraCyte™; 5: $4 \times 10^5$ AF-N cultured using a cell culture in TheraCyte™; and 6: $1.0 \times 10^6$ AF-N cultured using a cell culture in TheraCyte™)

As a result, when AF-N was cultured using the attached cell culture, the bFGF concentration increased along with the cell count of AF-N. However, when AF-N was cultured using the cell culture in TheraCyte™, a bFGF secretion did not increase along with the cell count of AF-N, and the bFGF concentration in the conditioned media were constantly maintained (FIG. 2).

This signifies that, similar to a general cell culture using the attached cell culture, the cytokine that having a hair-growing function secreted from the stem cells injected into TheraCyte™ pass through a TheraCyte™ membrane and are secreted to outside of TheraCyte™ in the case in which AF-N is cultured using the cell culture in TheraCyte™. Therefore, it was confirmed that TheraCyte™ does not restrict the hair-growing function and may be utilized as a means for transferring a hair growth solution.

Reasons for the bFGF secretion being constantly maintained without a significant change when AF-N is cultured using the cell culture in TheraCyte™ include the followings. 1) Because the stem cells grow inside TheraCyte™, which is a limited space, metabolism of the cells may be different in comparison to that of cells cultured using the attached cell culture; 2) Because TheraCyte™ is not only spatially limited but also has a limited path through which cytokine can be discharged, an amount of cytokine that can pass through the path within a given amount of time may be limited due to the bottleneck phenomenon of the path.

Therefore, whether the reason for constant bFGF concentration in the conditioned media when AF-N is cultured using the cell culture in TheraCyte™ is because an amount of cytokine capable of passing through the TheraCyte™ membrane is saturated was confirmed through an additional experiment.

EXPERIMENTAL EXAMPLE 2

Confirmation of Secretion of Cytokine Having a Hair-Growing Function from AF-N Injected into TheraCyte™

Whether the reason for the constant bFGF concentration in the conditioned media when AF-N was cultured using the cell culture in TheraCyte™ was because an amount of cytokine capable of passing through the TheraCyte™ membrane was saturated was confirmed, AF-N was cultured using the same method as in Experimental Example 1 to determine the number of stem cells to be injected into TheraCyte™ when transplanting in the mice, and concentrations of cytokines having a hair-growing function in the acquired conditioned media were measured. The cytokines measured here were bFGF, PDGF-AA, IGF, and Wnt7a, which are known as growth factors that promote hair growth.

As a result, similar to the case of bFGF, in the cases of PDGF-AA and Wnt7A, an amount of discharged cytokine increased along with the number of injected cells when cultured using the attached cell culture. Although an increase in the amount of cytokine was observed when AF-N was cultured using the cell culture in TheraCyte™, the increase was confirmed to be relatively small in comparison to the case of the attached cell culture.

Figure 3:
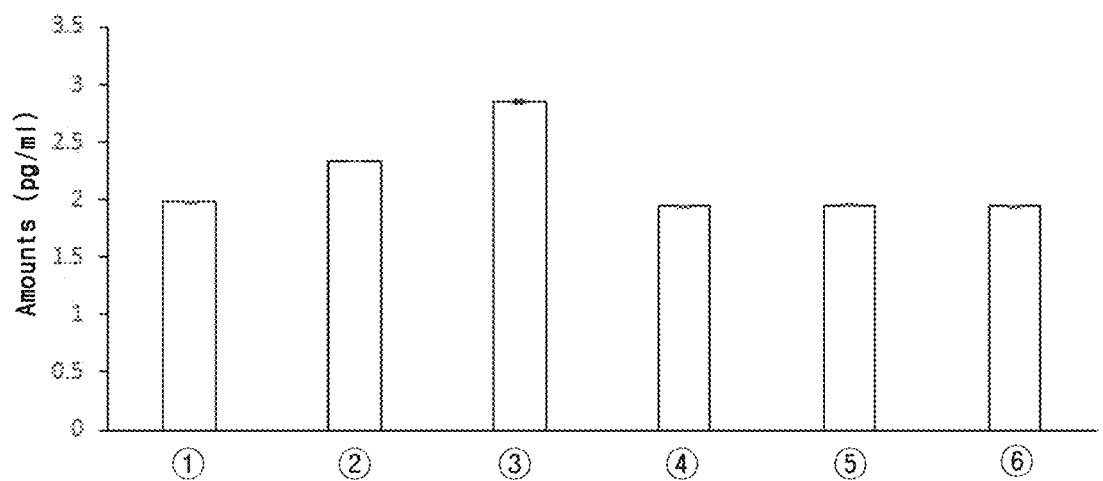
FIGS. 3 to 6 show concentrations of bFGF (FIG. 3), platelet-derived growth factor (PDGF)-AA (FIG. 4), an insulin-like growth factor (IGF) (FIG. 5), and Wnt7a (FIG. 6) in conditioned media according to culturing method (1: $1.0 \times 10^5$ AF-N cultured using an attached cell culture; 2: $4 \times 10^5$ AF-N cultured using an attached cell culture; 3: $1.0 \times 10^6$ AF-N cultured using an attached cell culture; 4: $1.0 \times 10^5$ AF-N cultured using a cell culture in TheraCyte™; 5: $4 \times 10^5$ AF-cultured using a cell culture in TheraCyte™; and 6: $1.0 \times 10^6$ AF-N cultured using a cell culture in TheraCyte™)
Figure 4:
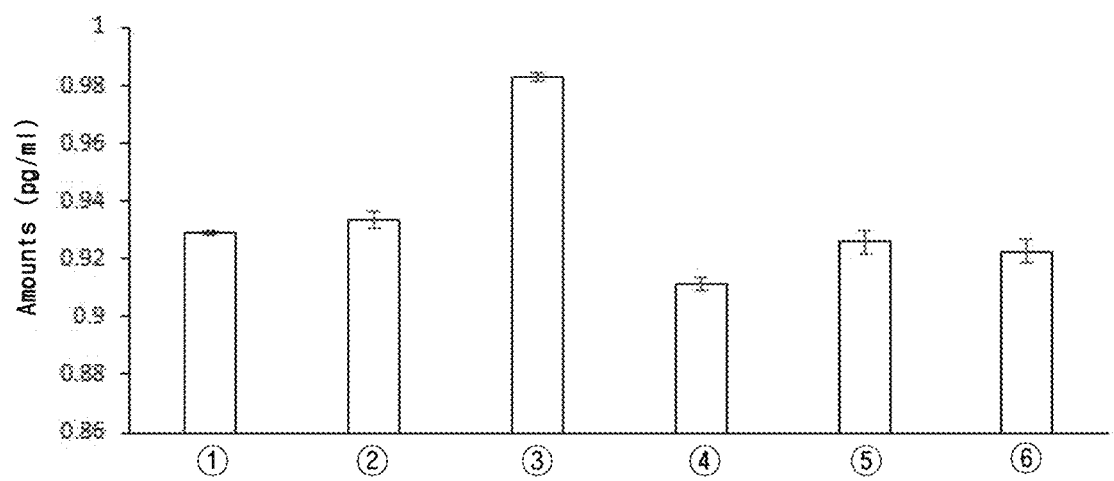
Figure 5:
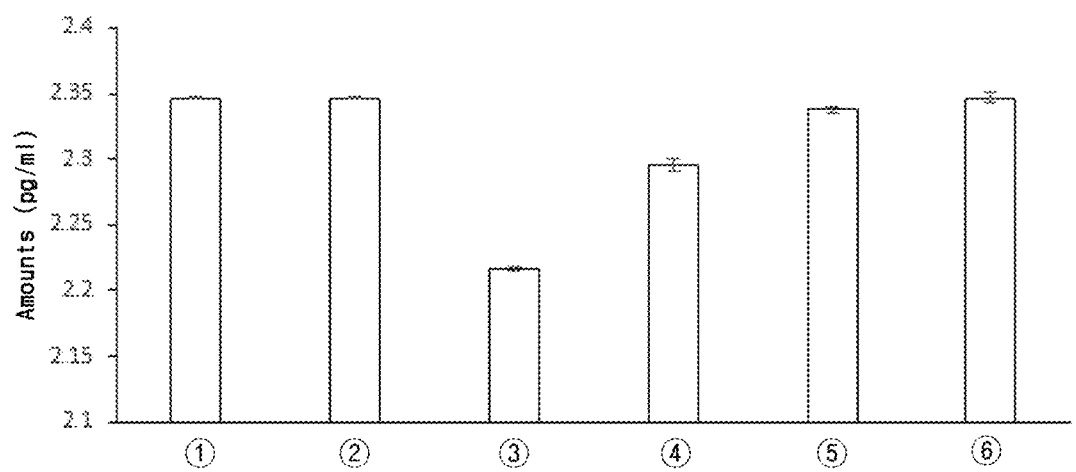
Figure 6:
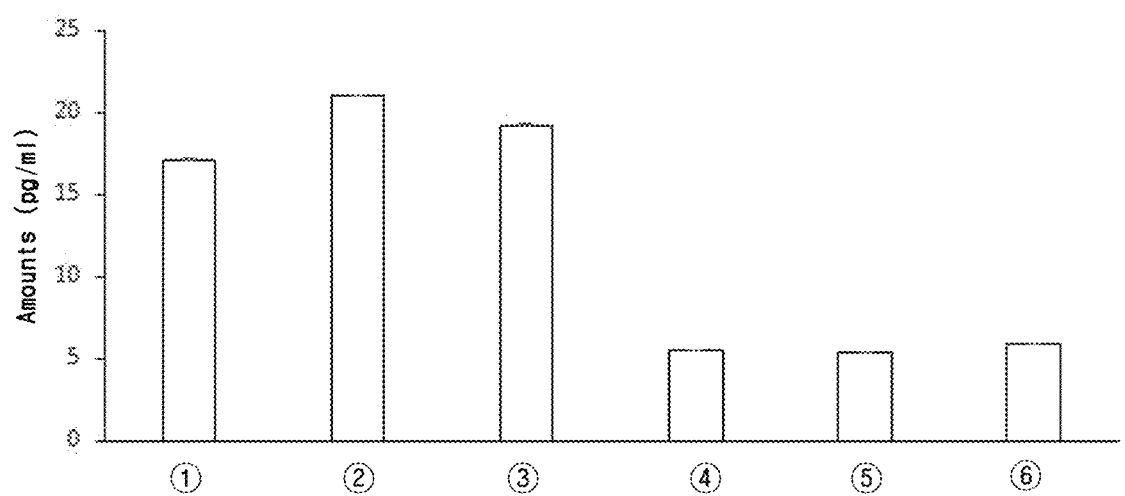

On the other hand, in the case of IGF, unlike in the cases of bFGF, PDGF-AA, and Wnt7a, the IGF concentration was observed as being constant and then decreasing regardless of an increase in the number of injected cells when cultured using the attached cell culture condition, and it was confirmed that the IGF concentration in the conditioned media constantly increased along with the number of injected cells when cultured using the cell culture in TheraCyte™ (FIG. 3: bFGF, FIG. 4: PDGF-AA, FIG. 5: IGF, FIG. 6: Wnt7a) (1: $1.0 \times 10^5$ AF-N cultured using the attached cell culture; 2: $4 \times 10^5$ AF-N cultured using the attached cell culture; 3: $1.0 \times 10^6$ AF-N cultured using the attached cell culture; 4: $1.0 \times 10^5$ AF-N cultured using the cell culture in TheraCyte™; 5: $4 \times 10^5$ AF-cultured using the cell culture in TheraCyte™; and 6: $1.0 \times 10^6$ AF-N cultured using the cell culture in TheraCyte™).

Therefore, it was confirmed that the path in TheraCyte™ through which cytokine may be discharged did not reach a saturated state. Consequently, it was determined that the reason for the cytokine concentration in the conditioned media not increasing along with the number of cells injected into TheraCyte™ was because the spatial limitation of TheraCyte™ affects metabolism of the stem cells.

On the basis of the above results, some measured values of cytokines having a hair-growing function increased along with the number of cells injected into TheraCyte™ in vitro, and because serum passes through the TheraCyte™ membrane and is supplied to the stem cells under in vivo condition, there was a possibility that the metabolism of the stem cells would be activated and more cytokines would be discharged. Therefore, further experiments were carried out by setting the number of cells to be injected into TheraCyte™ to be the largest possible number, $1.0 \times 10^7$. That is, the in vivo experiment afterwards was carried out by injecting $1.0 \times 10^7$ stem cells into TheraCyte™ and then transplanting TheraCyte™ in mice.

EXPERIMENTAL EXAMPLE 3

Evaluation of Viability of Cells in TheraCyte™

$1.0 \times 10^7$ stem cells of Examples 1 to 4 were injected in TheraCyte™, and then TheraCyte™ was transplanted in the skin of the C57BL/6 mice. Then, the transplanted TheraCyte™ was harvested after 14 days, and then the injected stem cells were separately evaluated using the CCK.

The CCK is capable of sensitively measuring cell viability using tetrazolium salt (WST-8) that exhibits high water solubility and changes color due to a formazan dye released by being reduced by NADP/NADPH dehydrogenase.

Also, (1) a case in which cell viability was measured using TheraCyte™ (bio-transplant container) (marked as theracyte) and (2) a case in which cell viability was measured right after $1.0 \times 10^7$ amniotic fluid derived mesenchymal stem cells (AF) were injected into TheraCyte™ (a positive control group, marked as positive) were compared. In (1), instead of injecting AF into TheraCyte™ and transplanting TheraCyte™ in the mice, viability of stem cells was measured right after the AF were injected into TheraCyte™ In (2), without introducing the Nanog gene, amniotic fluid stem cells cultured under normoxia were injected into TheraCyte™. That is, the above (1) and (2) are groups in which TheraCyte™ was not transplanted in the mice.

As a result, all of the amniotic fluid stem cells of Examples 1 to 4 exhibited higher cell viability measurement values in comparison to when measuring only TheraCyte™ without injected stem cells. This signifies that the stem cells are alive even 14 days after transplantation. Also, this signifies that the injected stem cells were protected by the TheraCyte™ membrane and were unaffected by immune rejection.

When the results of Examples 1 to 4 were compared, the reprogrammed amniotic fluid stem cells exhibited higher viability than the amniotic fluid stem cells, and the stem cells grown under hypoxia exhibited higher viability than the stem cells grown under normoxia.

Figure 7:
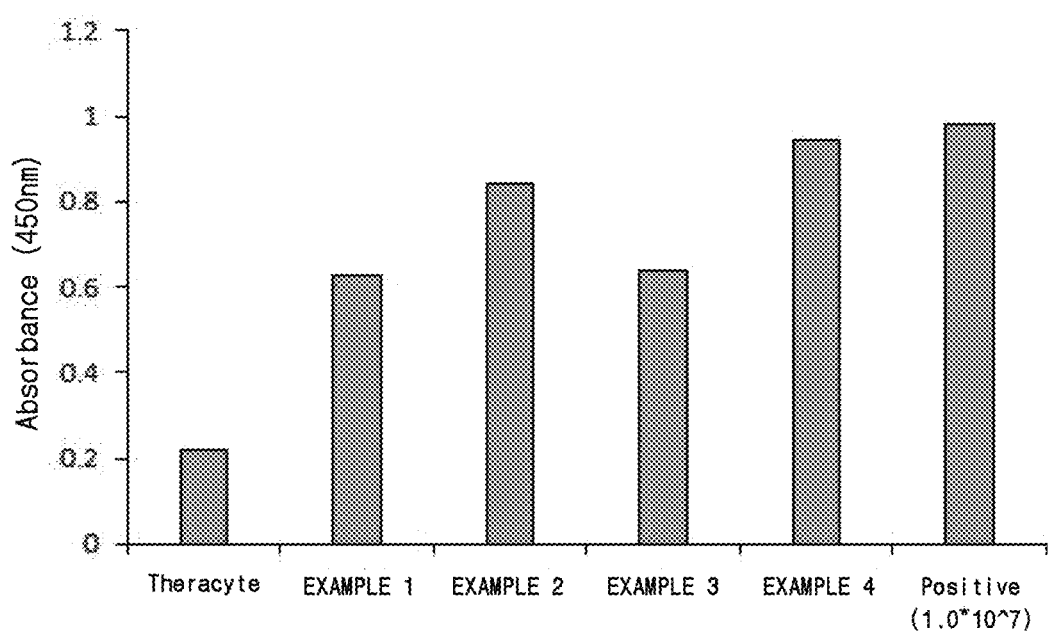
FIG. 7 shows cell survival rates when stem cells of Examples 1 to 4 are injected into TheraCyte™.

In the case of the amniotic fluid stem cells of Example 3, although cell viability was measured 14 days after transplantation, the viability was not much different from that in Example 1 in which stem cells were grown under normoxia. Therefore, the reprogrammed amniotic fluid stem cells cultured under hypoxia were determined to be the most suitable for developing treatment for hair loss (FIG. 7).

EXPERIMENTAL EXAMPLE 4

The C57BL/6 mice mostly used for confirming functions of hair have a characteristic that their skin color is determined by an amount of melanin pigment in follicles due to melanin cells that form pigments not being present in the epidermis and present only in the follicles. Because synthesis of melanin pigments in the follicles occur only during the growing phase of hair, the skin color turns black in the growing phase, and the skin color turns pink during the transitional phase and the resting phase in which the synthesis of melanin pigments does not occur. Therefore, there is an advantage in that hair growth cycle can be confirmed from skin color without histological analysis of skin.

Figure 8:
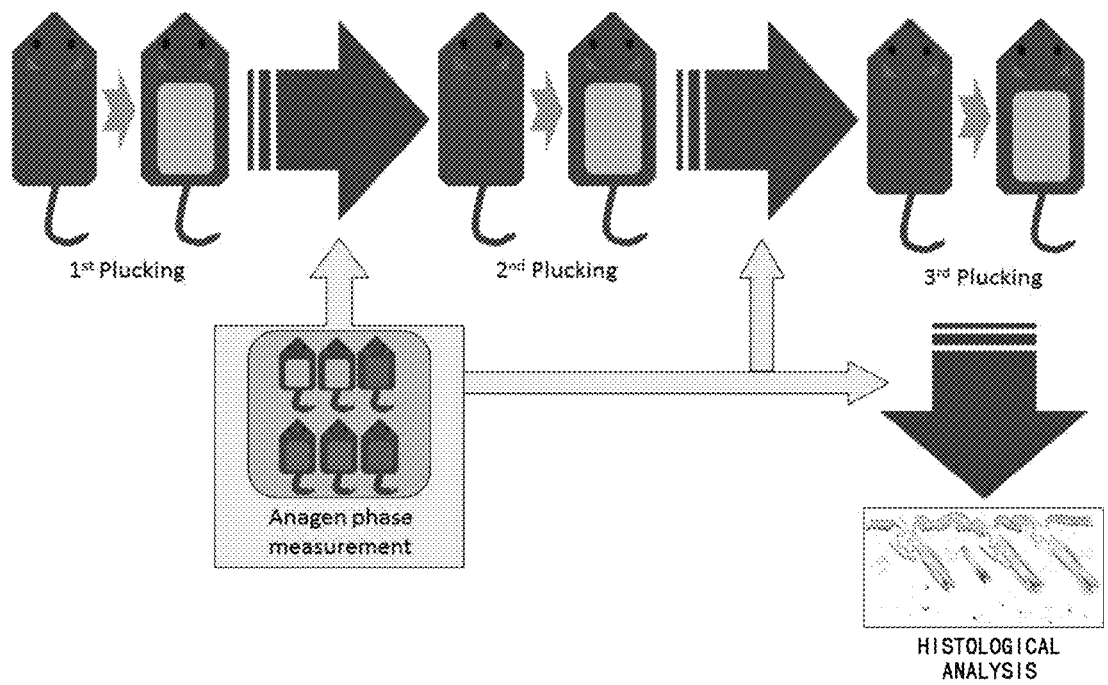
FIG. 8 is a schematic diagram illustrating a process of using mice to confirm a vital function of TheraCyte™ into which the stem cells are injected.

In the present disclosure, $1.0 \times 10^7$ amniotic fluid stem cells of Examples 1 to 4 were injected in TheraCyte™, a first plucking was performed, and then TheraCyte™ was transplanted in the C57BL/6 mice undergoing the second anagen phase to evaluate a hair-growing function. Here, the mice not treated with any sample (untreated group) was set as a control group, and a hair growth pattern was observed. FIG. 8 is a schematic diagram of an in vivo process of confirming the hair-growing function in the mice.

Figure 9:
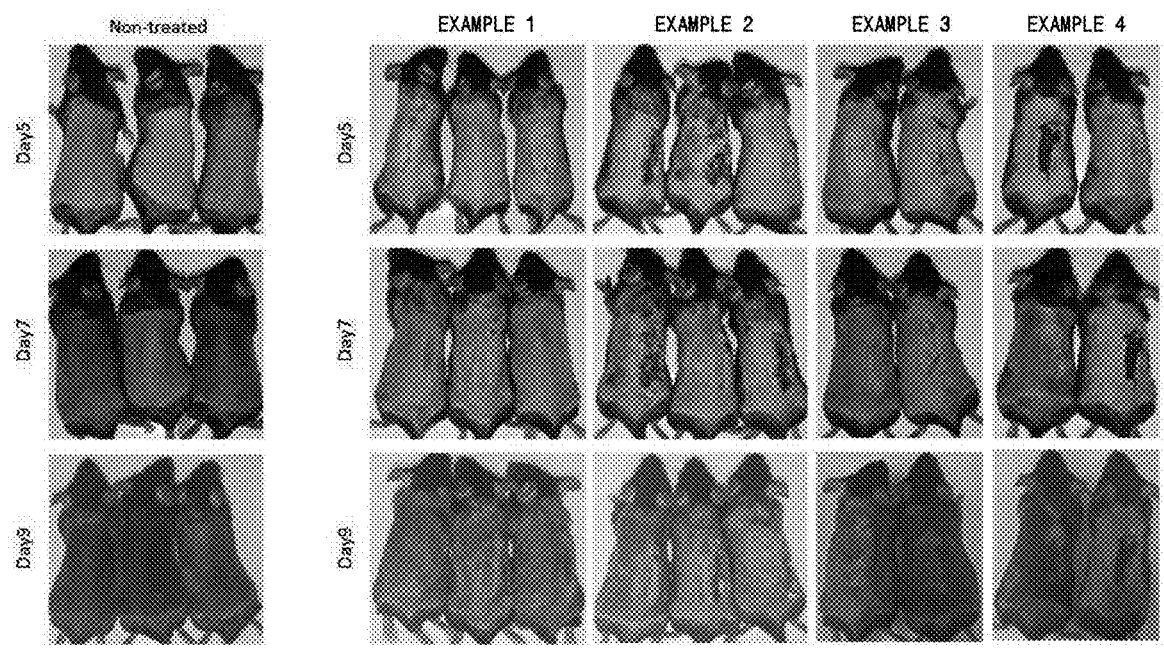
FIG. 9 shows photographs of confirming a hair growth inducing effect by transplanting TheraCyte™ after first plucking.

As a result, it was shown that the hair growth promoting function was higher in the case in which the amniotic stem cells of Examples 3 and 4 were injected into TheraCyte™ and TheraCyte™ was transplanted in comparison to other experimental groups (Examples 1 and 2, and the untreated control group) (FIG. 9).

This may be interpreted as a result of an increase in the cytokine secretion under hypoxia combinatorially affecting the hair-growing function. Because a large wound was formed on the experimental animals due to transplantation of TheraCyte™, and this can affect the hair-growing function, plucking of hair was performed after the wound was healed, and then the hair-growing function was re-evaluated.

Figure 10:
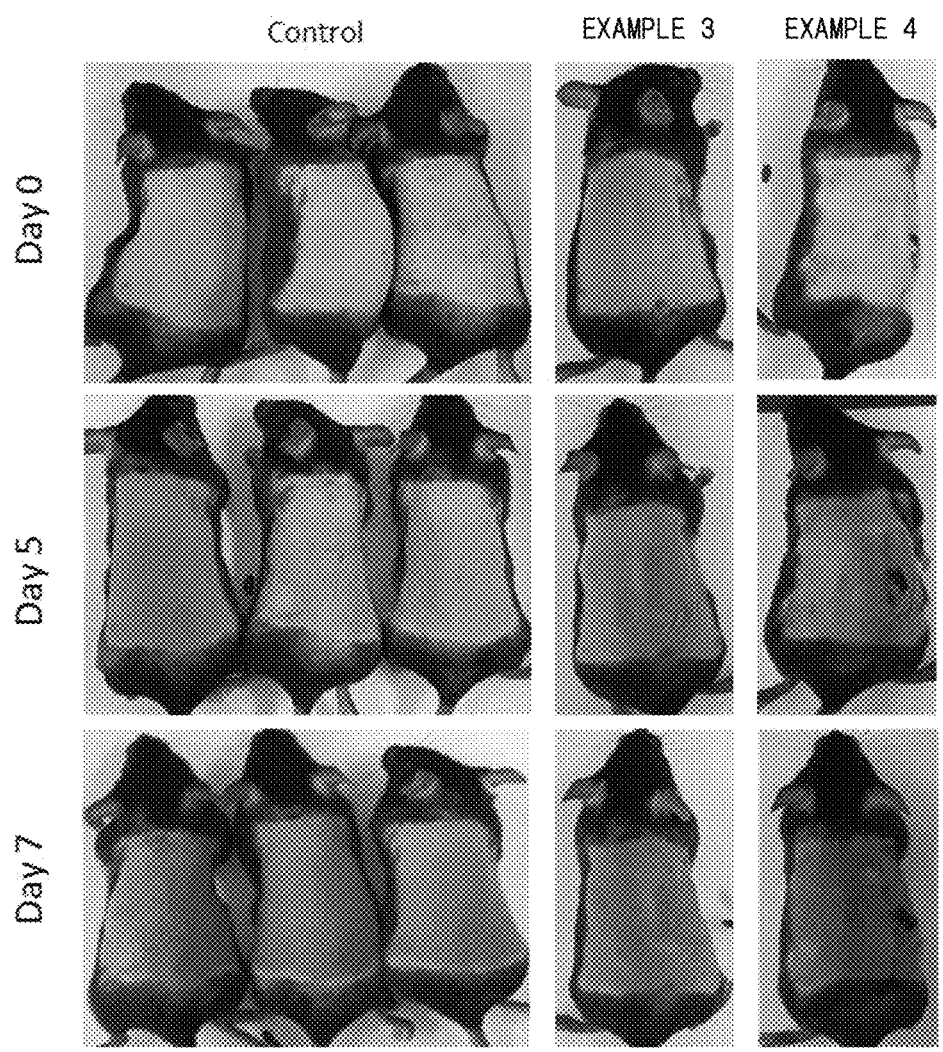
FIG. 10 shows photographs of confirming a hair growth inducing effect by transplanting TheraCyte™ after second plucking. Here, only hypoxia-cultured stem cells from which the hair growth inducing effect was confirmed were compared.

As a result of observing after the plucking was performed after the wound was healed as determined above, anagen induction was more clearly exhibited in comparison to the control group as in the case in which the first plucking was performed after the amniotic fluid stem cells of Examples 3 and 4 were injected in TheraCyte™ and TheraCyte™ was transplanted from $7^{th}$ day after the second plucking (FIG. 10).

Figure 11:
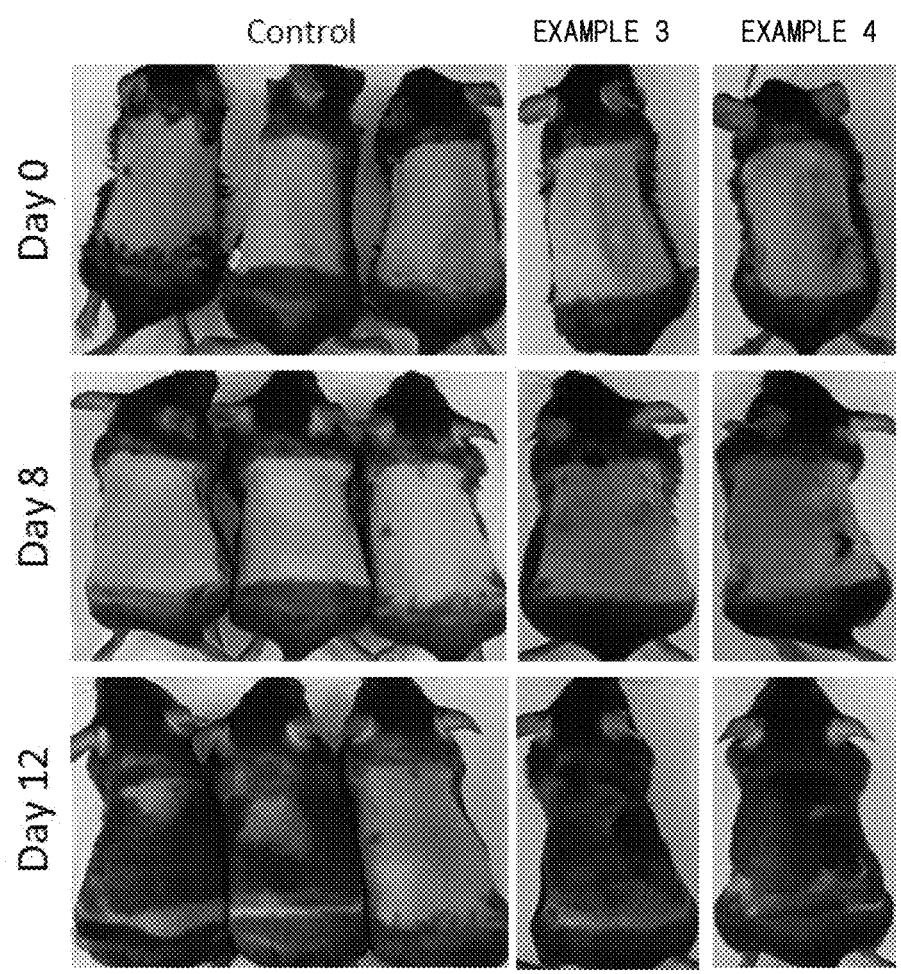
FIG. 11 shows photographs of confirming a hair growth inducing effect by transplanting TheraCyte™ after third plucking. Here, only hypoxia-cultured stem cells from which the hair growth inducing effect was confirmed were compared.

Also, a third plucking was performed, and a hair induction effect was observed. A result similar to those after the first and second plucking were exhibited. That is, when the stem cells of Examples 3 and 4 were injected into TheraCyte™ and the TheraCyte™ was transplanted, a difference in anagen induction in comparison to the control group was exhibited 8 days after the transplantation, and the difference became clearer 12 days after the transplantation. Also, a size of an area undergoing the anagen phase was observed to be larger in comparison to the cases of transplanting TheraCyte™ after the first and second plucking. Particularly, it was confirmed that the case of injecting reprogrammed amniotic fluid stem cells of Example 4 exhibited a larger increase in the anagen area in comparison to Example 3 (FIG. 11).

Therefore, it is confirmed that the hair induction effect can be consistently maintained by transplanting a TheraCyte™ in which stem cells were injected. Especially, the case of injecting reprogrammed amniotic fluid stem cells cultured under hypoxia of Example 4.

EXPERIMENTAL EXAMPLE 5

A few control groups were added to the experimental groups of Experimental Example 4 above, and the experiments were carried out in the same manner. Specifically, a case in which only TheraCyte™ was transplanted without injection of stem cells into TheraCyte™ was set as an additional negative control group (Theracyte-only) to confirm an influence of a wound formed due to the transplantation of TheraCyte™ on the hair-growing function. Also, a case in which reprogrammed amniotic fluid stem cell culture media (the number of stem cells: $1.0 \times 10^7$) was smeared in the skin of the mice was used as a control group (smear). Also, a wound clip, which is suitable for suturing a large wound, was used to efficiently suture a wound. Except for the above, the experiment was carried out with the same method and conditions as Experimental Example 4. As in Experimental Example 4, the experiment was carried out after calculating the number of stem cells of Examples 1 to 4 to be injected into TheraCyte™ to be about $1.0 \times 10^7$. TheraCyte™ was transplanted in the C57BL/6 mice undergoing the second anagen phase after the first plucking.

Figure 12:
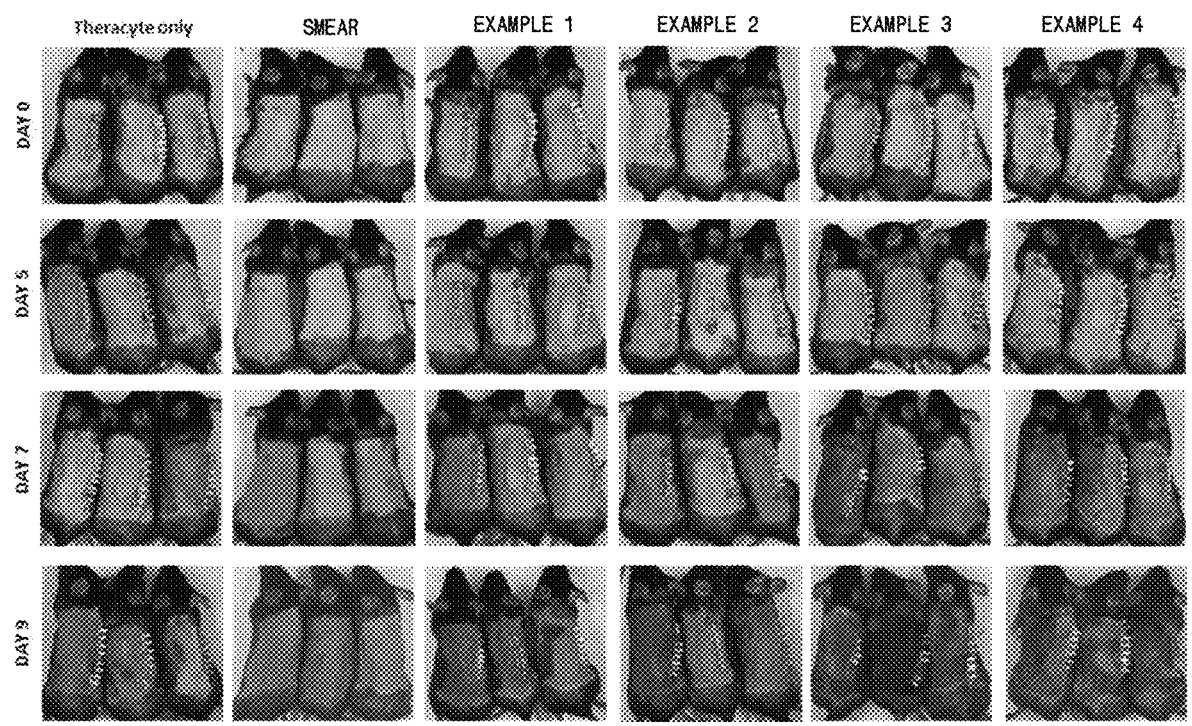
FIG. 12 shows photographs confirming a hair growth inducing effect from transplanting TheraCyte™ after adding a control group and performing a first plucking.

As a result, as in Experimental Example 4, it was confirmed that a hair-growing effect of the stem cells could be continuously maintained when TheraCyte™ was used, and particularly, it was confirmed that the hair-growing effect was the greatest when the reprogrammed amniotic fluid stem cells of Example 4 were injected into TheraCyte™ and TheraCyte™ was transplanted (FIG. 12).

EXPERIMENTAL EXAMPLE 6

The above experimental results confirmed that the reprogrammed amniotic fluid stem cells injected into TheraCyte™ had a hair-growing function. Therefore, a hair-growing ability was evaluated using aged mice with hair loss having a similar characteristic as the elderly, a majority of whom actually suffer from hair loss.

For this experiment, 13-week-old or older C57BL/6 mice were prepared. The mice were determined as suitable for the experiment due to undergoing spontaneous hair loss without being separately treated and the ease with which their hair growth cycle can be determined (McMahon W M, Sundberg J P. Animal Models and Biomedical Tools, ed. Sundberg J P, pp. 493-497. CRC Press, Boca Raton, Fla., 1994.).

The specific experimental method was the same as those in Experimental Examples 4 and 5. In this experiment, a case in which only TheraCyte™ was transplanted without injected stem cells into TheraCyte™ was set as an additional negative control group (Theracyte-only) to confirm an influence of a wound formed due to the transplantation of TheraCyte™ on the hair-growing function. Also, a case in which the stem cell culture media (the number of stem cells: $1.0 \times 10^7$) of Example 4 was smeared in the skin of the mice was used as a control group (Example 4-smear). Also, as in Experimental Example 4, the experiment was carried out after calculating the number of stem cells of Examples 2 and 4 to be injected into TheraCyte™ to be about $1.0 \times 10^7$. TheraCyte™ was transplanted in the C57BL/6 mice undergoing the second anagen phase after the first plucking.

Figure 13:
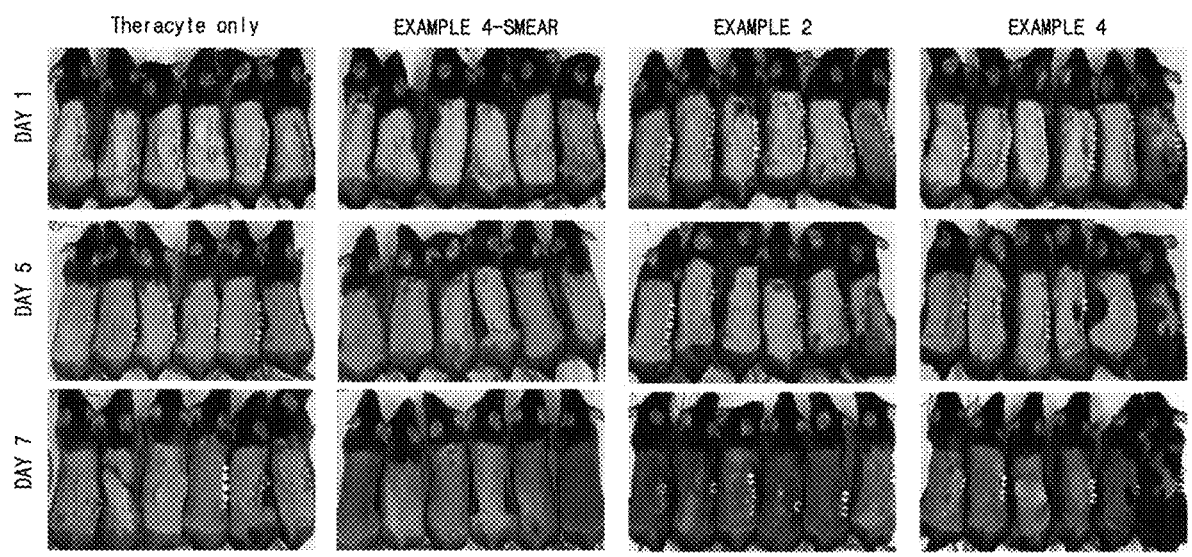
FIG. 13 shows photographs comparing induction of the growth phase of hair by transplanting TheraCyte™ after a first plucking of an aged mouse model.

As a result, as the results of the previous Experimental Examples, it was confirmed that anagen induction more rapidly occurred with the stem cells of Examples 2 and 4 injected into TheraCyte™ in comparison to the Theracyte-only control group and the group smeared with the stem cell culture media of Example 4 (FIG. 13). This signifies that the reprogrammed amniotic fluid stem cells have a superior hair-growing function than the amniotic fluid stem cells.

EXPERIMENTAL EXAMPLE 7

As a result of Experimental Example 6 above, it was confirmed that TheraCyte™ including the reprogrammed amniotic fluid stem cells of the present disclosure was also effective in the aged mice also. To confirm a difference in the anagen induction function between the control group and the mice aged even further, a second plucking experiment was carried out using 19-week-old mice (the existing 13-week-old mice of Experimental Example 6 above were used again 6 weeks after the experiment using the 13-year-old mice, which was when the anagen phase began again).

Figure 14:
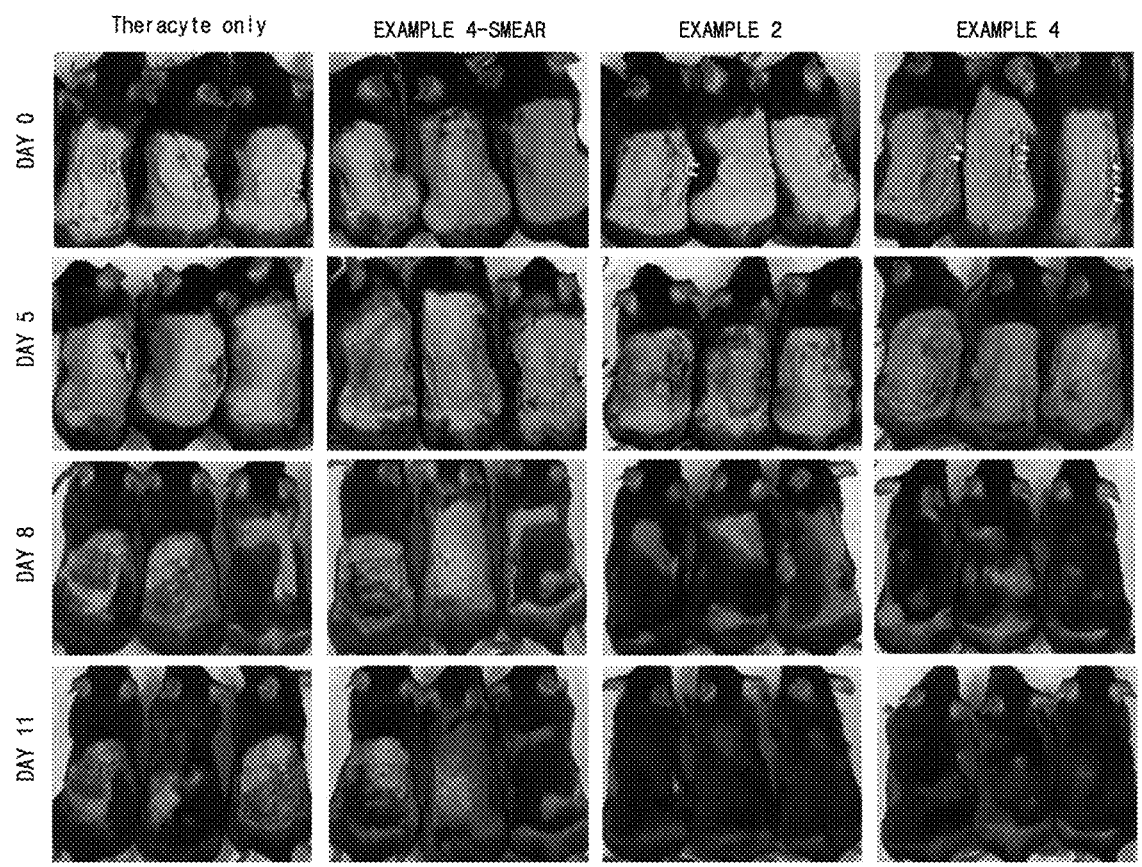
FIG. 14 shows photographs of comparing induction of the growth phase of hair by transplanting TheraCyte™ after a second plucking of an aged mouse model.

As a result, a clearer result was exhibited in comparison to Experimental Example 6. It was determined that this was due to a large difference in anagen induction over time between the groups, in which TheraCyte™ was transplanted, due to continuous secretion of hair-growing cytokines and functional expression thereof in comparison to the control group, in which the anagen induction was partially slowed down due to progress of hair loss caused by aging of the mice. This implies that the secretome of cells present in TheraCyte™ is more effective in growing hair than applying the conditioned media on the skin. Like the result of Experimental Example 6, the hair-growing effect was the greatest in the groups of Example 3 (theracyte) and Example 4 (theracyte), was the next greatest in the Example 4-smear group, and was the smallest in the Theracyte-only group (FIG. 14).

EXPERIMENTAL EXAMPLE 8

Above, whether the amniotic fluid stem cell group was alive was confirmed using the CCK. To re-confirm this, an experiment for confirming a living state of the amniotic fluid stem cell group inside TheraCyte™ was performed. Here, a sample from the $7^{th}$ day in Experimental Example 7 was used as a TheraCyte™ sample, and Hematoxylin & Eosin (H&E) staining was performed by dissecting the inside of TheraCyte™.

Figure 15:
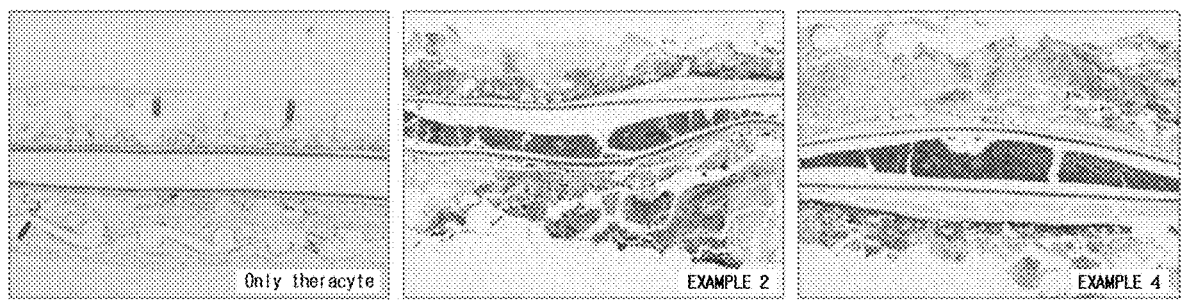
FIG. 15 shows forms of reprogrammed amniotic fluid stem cells inside TheraCyte™ nine days after being transplanted in a tissue.

As a result, it was confirmed that a tissue in which only TheraCyte™ was transplanted (Theracyte-only) was empty on the inside. Conversely, it was confirmed that stem cells were organized and formed inside TheraCyte™ in which the stem cells of Examples 2 and 4 were injected (FIG. 15). In this way, it was proven that the cells grew and survived for about 6 weeks or more and continuously performed their functions.

EXPERIMENTAL EXAMPLE 9

The anagen induction was proven by the exterior of the aged mice in Experimental Examples 6 and 7. Therefore, through a histological analysis, it was confirmed that follicles were actually formed. For this, on the fifth day of carrying out Experimental Example 7, skin tissue of the aged mice was sampled and analyzed.

Figure 16:
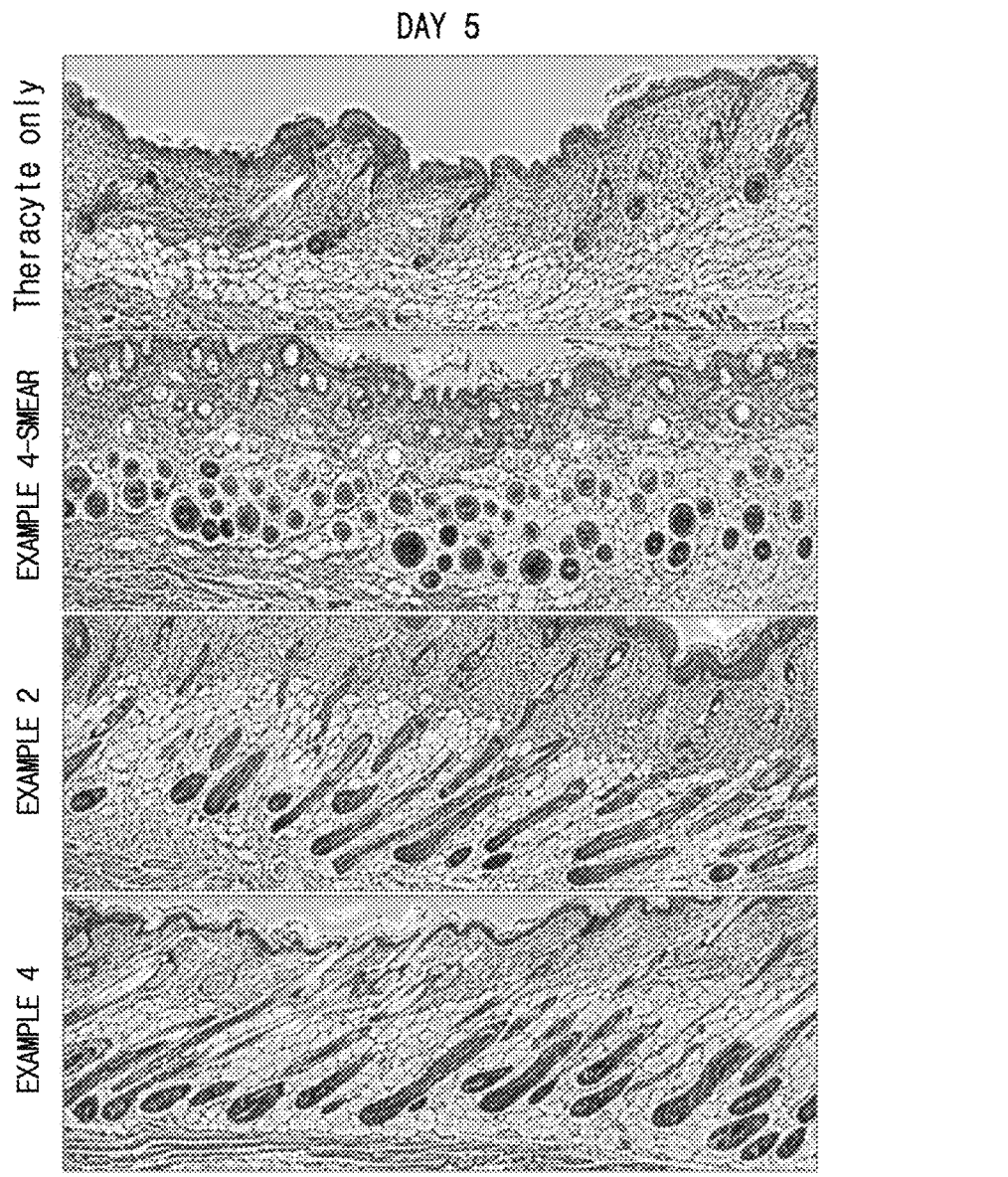
FIG. 16 shows results of analyzing differences in follicle formation in skin tissues of each group.

As a result, a large amount of follicular tissues were confirmed in the skin tissues of the TheraCyte™ group (Examples 2 and 4), and, also in terms of the anagen phase, it was confirmed that an amount of follicular forms in the late anagen phase was larger than an amount of follicular forms in the early anagen phase. Conversely, it was confirmed that, although multiple human hair follicle dermal papilla (HFDP) cell groups prone to become follicles were present in the Example 4-smear group, the cell groups were in a relatively earlier phase of the anagen phase, and the anagen induction function was somewhat inferior in comparison to the Theracyte groups (FIG. 16).

EXPERIMENTAL EXAMPLE 10

To re-confirm the result of Experimental Example 9 above, alkaline phosphatase (AP) staining of the skin tissues were performed to measure HFDP cell activity. In this experiment, a larger and clearer positive section resulting from AP staining indicated higher cell activity with respect to hair production.

Figure 17:
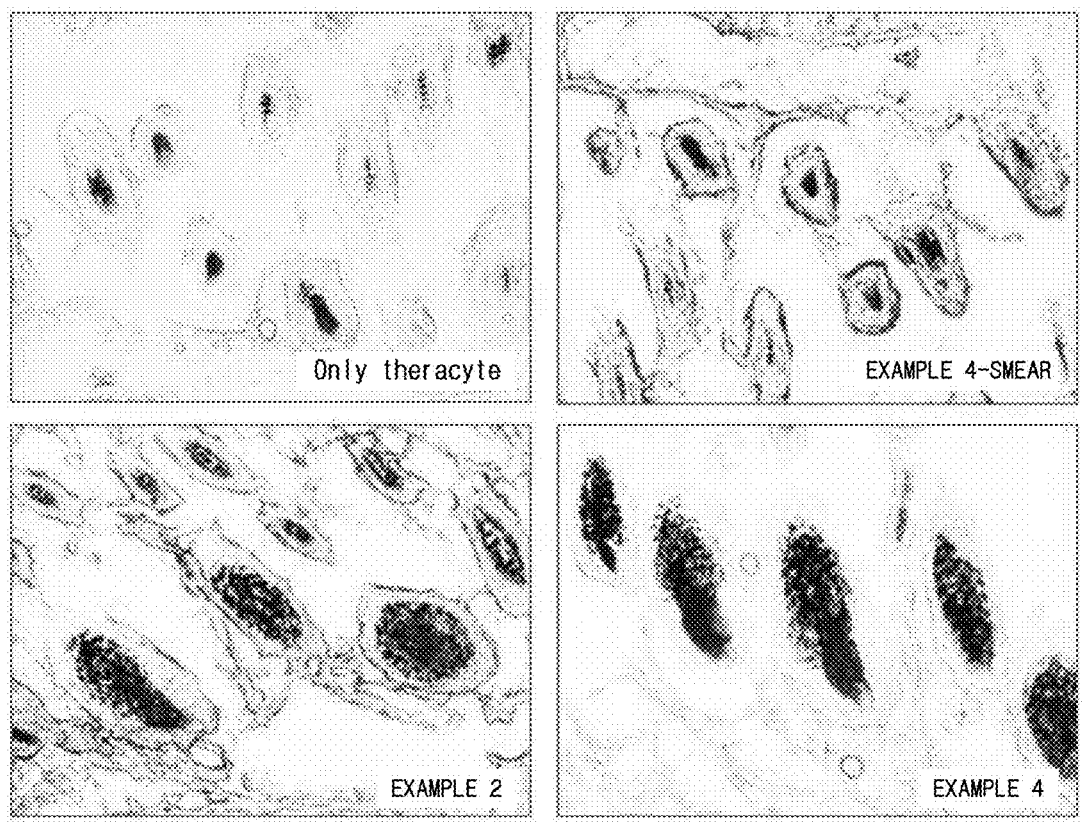
FIG. 17 shows the results of measuring human hair follicle dermal papilla (HFDP) cell activity using alkaline phosphatase (AP) staining of the skin tissues of each group.

As a result, it was confirmed with visual inspection that the HFDP cell activity of the Theracyte groups into which the stem cells of Examples 2 and 4 were injected was significantly higher in comparison to the Theracyte-only group and the group smeared with the stem cells of Example 4 (FIG. 17).

Therefore, it was confirmed that TheraCyte™ frees the stem cells from an immune reaction and improves the function of the stem cells at the same time through the paracrine effect.

According to the present disclosure, an implant of the present invention is transplanted in a living body and secretes components having a hair-growing function, thereby allowing promotion of hair growth and alleviation/treatment of hair loss for a long period.

The scope of the present disclosure is defined by the claims below rather than the detailed description, and all changes and modifications derived from the sense and the scope of the claims and their equivalents should be construed as belonging to the scope of the present disclosure.

What is claimed is:

1. A transplantation implant for treating or alleviating hair loss or for promoting hair growth comprising:
   a container having a permeable membrane and stem cells disposed within the container, wherein the stem cells have an ability of secreting a cytokine having a hair-growing function, wherein the stem cells are reprogrammed amniotic fluid stem cells, and wherein the stem cells are stem cells cultured under hypoxia at an oxygen concentration of 0.05% to 5%.

2. The transplantation implant of claim 1, wherein the cytokine having the hair-growing function is selected from the group consisting of a basic fibroblast growth factor (bFGF), a platelet-derived growth factor (PDGF)-AA, an insulin-like growth factor (IGF), and Wnt7a.

3. The transplantation implant of claim 1, wherein the transplantation implant comprises $1.0 \times 10^3$ to $1.0 \times 10^{10}$ stem cells.

4. The transplantation implant of claim 1, wherein the transplantation implant is transplanted under scalp.

5. The transplantation implant of claim 1, wherein the hair loss is due to aging.

6. A method of preparing the transplantation implant of claim 1, the method comprising injecting the stem cells having an ability to secrete a cytokine having a hair-growing function into the container to produce the transplantation implant.

7. A method of treating or alleviating hair loss, the method comprising transplanting the transplantation implant of claim 1 into a living body.

8. The transplantation implant of claim 1, wherein the permeable membrane permits oxygen and nutrients to be supplied to the implant.

9. The transplantation implant of claim 1, wherein the permeable membrane permits secretion of the cytokine out of the implant.

10. The transplantation implant of claim 1, wherein the permeable membrane has a hole size through which cells are unable to pass.

11. The transplantation implant of claim 1, wherein the permeable membrane is biocompatible.

12. The transplantation implant of claim 1, wherein the permeable membrane comprises polyurethane.

13. The transplantation implant of claim 1, wherein the stem cells are cultured in an oxygen concentration of 0.1% to 3%.

14. The transplantation implant of claim 1, wherein the reprogrammed amniotic fluid-derived stem cells are prepared by introducing a Nanog gene.

15. A transplantation implant for treating or alleviating hair loss or for promoting hair growth comprising:
   a container having a permeable membrane and stem cells disposed within the container, wherein the stem cells have an ability of secreting a cytokine having a hair-growing function,
   wherein the stem cells are reprogrammed amniotic fluid-derived stem cells prepared by introducing a Nanog gene, wherein the stem cells are cultured under hypoxia at an oxygen concentration of 0.1% to 3%,
   wherein the permeable membrane comprises a thin-film polymer, wherein the permeable membrane permits oxygen and nutrients to be supplied to the implant, wherein the permeable membrane permits secretion of the cytokine out of the implant and wherein the permeable membrane has a hole size through which cells are unable to pass.

* * * * *